United States Patent [19]

Hay

[11] 4,253,453
[45] Mar. 3, 1981

[54] SELECTOR VALVE FOR ANESTHESIA MACHINE

[75] Inventor: Wayne W. Hay, Madison, Wis.

[73] Assignee: Airco, Inc., Montvale, N.J.

[21] Appl. No.: 86,385

[22] Filed: Oct. 19, 1979

[51] Int. Cl.$^3$ .......................................... A61M 17/00
[52] U.S. Cl. .............................. 128/200.19; 128/274; 128/205.24; 137/625.47; 210/340
[58] Field of Search ...................... 128/200.11, 200.13, 128/200.14, 200.16, 200.17, 200.18, 200.19, 200.21, 200.22, 203.12, 203.14, 203.25, 203.28, 204.14, 205.11, 205.17, 205.24, 274; 137/625.47, 625.29, 625.32; 210/340, 341

[56] References Cited

U.S. PATENT DOCUMENTS

| | | | |
|---|---|---|---|
| 1,071,432 | 8/1913 | Kelley | 128/200.19 X |
| 1,578,383 | 3/1926 | Bayles et al. | 128/274 X |
| 1,704,045 | 3/1929 | Jackson | 128/200.11 X |
| 1,759,927 | 5/1930 | Zwicky | 210/340 X |

FOREIGN PATENT DOCUMENTS

| | | | |
|---|---|---|---|
| 255258 | 11/1912 | Fed. Rep. of Germany | 128/200.11 |
| 778787 | 7/1957 | United Kingdom | 128/203.25 |
| 1193522 | 6/1970 | United Kingdom | 128/203.28 |

*Primary Examiner*—Henry J. Recla
*Attorney, Agent, or Firm*—Roger M. Rathbun; Larry R. Cassett; Edmund W. Bopp

[57] ABSTRACT

A selector valve for providing a choice of one of two vaporizers for use in administering an anesthetic to a patient is disclosed in connection with a manifold for receiving the vaporizers.

The selector valve has three positions, wherein the user can utilize one of two vaporizers or place the valve in an off position when neither vaporizer is in the circuit providing a flow of gas to the patient.

One of the features comprises a positive position means where the selector valve cannot inadvertently be placed in any position intermediate any two of the three positions so that only one of the three defined positions may be selected. Also, in the off position, leakage is prevented into the gas stream to the patient of anesthetic vapors from either of the vaporizers mounted to the manifold by closing both the inlet to and the outlet from both such vaporizers. Further, in the event one vaporizer is selected for use, the remaining vaporizer also has its inlet and outlet closed such that no inadvertent leakage of anesthetic vapor from the "off" vaporizer can reach the path of gas proceeding through the "on" vaporizer and selector valve to the patient.

The means of connection and sealing means within the selector valve further are designed to insure that any seal leakage due to wear will cause the leaking anesthetic vapors to vent to atmosphere and not leak into one of the other active gas paths to the patient.

6 Claims, 10 Drawing Figures

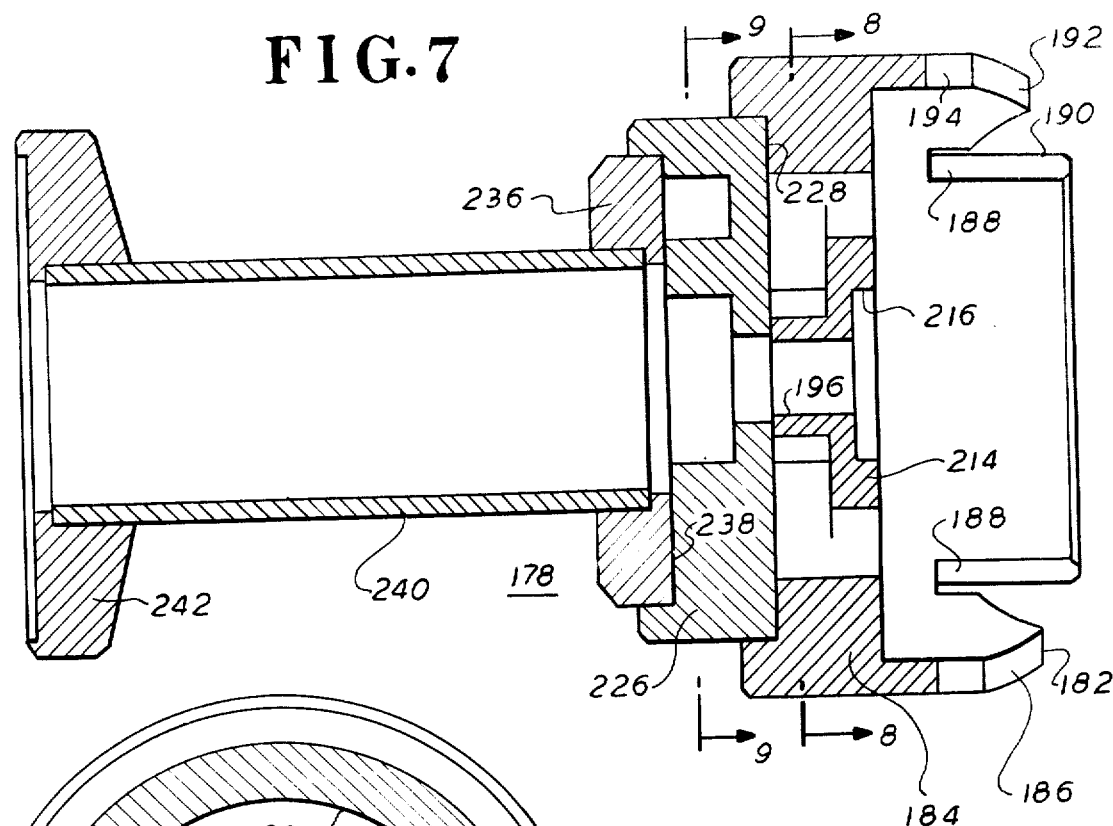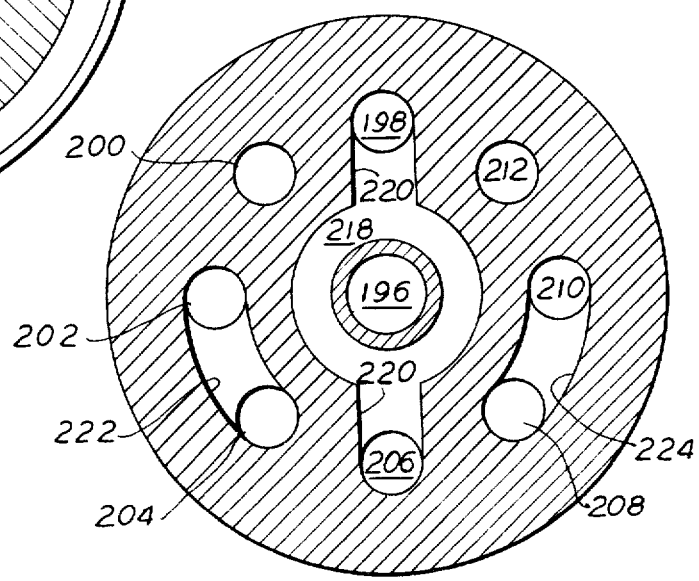

SELECTOR VALVE FOR ANESTHESIA MACHINE

BACKGROUND OF THE INVENTION

This invention relates generally to anesthesia machines used to administer an anesthetic agent to a patient for anesthetizing the same.

Typically, such machines combine valving, flowmeters and needle valves to deliver nitrous oxide and/or oxygen to the patient and also have the facility for passing the gas (oxygen or oxygen-nitrous oxide) through an anesthetic vaporizer of the calibrated type, such that the gas picks up anesthetic vapor of a predetermined precise proportion. The gas thus contains a volatile and potent anesthetic agent for carrying the patient down to surgical anesthesia levels.

Such anesthesia machines normally allow a selection of the volatile, liquid anesthetic and, thus, provide suitable mounting means and the necessary valving to allow an operator to choose the anesthetic agent he intends to use. Common among such anesthetic agents are halothane and enflurane, and it is not unusual to have a vaporizer available for ready use for administration of halothane and a vaporizer for enflurane.

One difficulty in selector valves for choosing between a selection of anesthetic agents and the various flow paths and connections associated therewith, is that the liquid anesthetic agents, being volatile, continually emit vapor that may inadvertently seep into the flow of oxygen or oxygen-nitrous oxide when the selector valve is actually in the off position.

Similarly, when two anesthetic vaporizers are potentially in the circuit, it is a further problem that the operator has selected one anesthetic, yet vapors from the other anesthetic may seep into the flow of gas to the patient. In any case, the seepage of unknown quantities of an anesthetic agent to the patient is obviously undesirable.

In prior selector valves, there was, in some cases, the further potential problem that the operator might position, either by accident or by purpose, the selector valve in some intermediate position, that is, between a positive selection of a particular anesthetic vaporizer and the off position when no anesthetic vaporizer is in the circuit to the patient. In such case, again, the actual flow of anesthetic agent to the patient becomes unknown and, in view of the need to have a continuous, very accurate knowledge of the exact vapor concentration to the patient, the mid-positioning is also extremely undesirable.

SUMMARY OF THE INVENTION

The anesthesia machine of the present invention features a selector valve and mounting manifold for anesthetic vaporizers.

The manifold is specially adapted to receive a plurality of vaporizers which plug into the manifold in a manner facilitating ease of engagement and removal. As a vaporizer is attached to such manifold, it automatically aligns with inlet and outlet ports that serve to bring gas to the anesthetic vaporizer and receive gas and anesthetic vapor therefrom. Channels are provided in the manifold to channel the gas streams to and from each vaporizer and such channels lead to a selector valve that can be operated to select one of the vaporizers to allow flow of gas thereto.

As one vaporizer is selected by use of the selector valve, the other vaporizer has its inlet channel for receiving gas closed by the selector valve and also has its outlet channel of the non-used vaporizer closed such that any vapors that are given off by anesthetic within the non-used vaporizer cannot find their way into the gases being delivered through the selector valve to the patient.

The same is true when the selector valve is placed in the off position when no anesthetic vaporizer is in the circuit delivering gas to the patient. In such position, gas to the selector valve passes directly therethrough and is delivered to the patient, yet the valve effectively closes passageways to and from the vaporizers, thus preventing stray, undesirable anesthetic vapors that may be present in the vaporizers from becoming mixed with the stream of gases to the patient.

A further feature of the selector valve is that it is provided with a means to prevent the valve from being set to an intermediate position, that is, between any two positions. The valve has positive positions for selecting either vaporizer and for using neither vaporizer. In the event an attempt, albeit inadvertent, is made to leave the selector valve in any but one of the positive positions, the valve will automatically lodge itself in one of such positions, thus the user cannot leave the valve in some alternate position.

BRIEF DESCRIPTION OF THE DRAWINGS

The invention is diagrammatically illustrated, by way of example, in the drawings appended hereto, in which:

FIG. 7 is a cross-sectional view of a further component of the selector valve of FIG. 4;

FIG. 8 is a cross-sectional view of the component of FIG. 7 taken along the lines 8—8;

FIG. 9 is a cross-sectional view of the component of FIG. 7 taken along the lines 9—9.

DETAILED DESCRIPTION OF THE INVENTION

Figures 1, 2, 10:
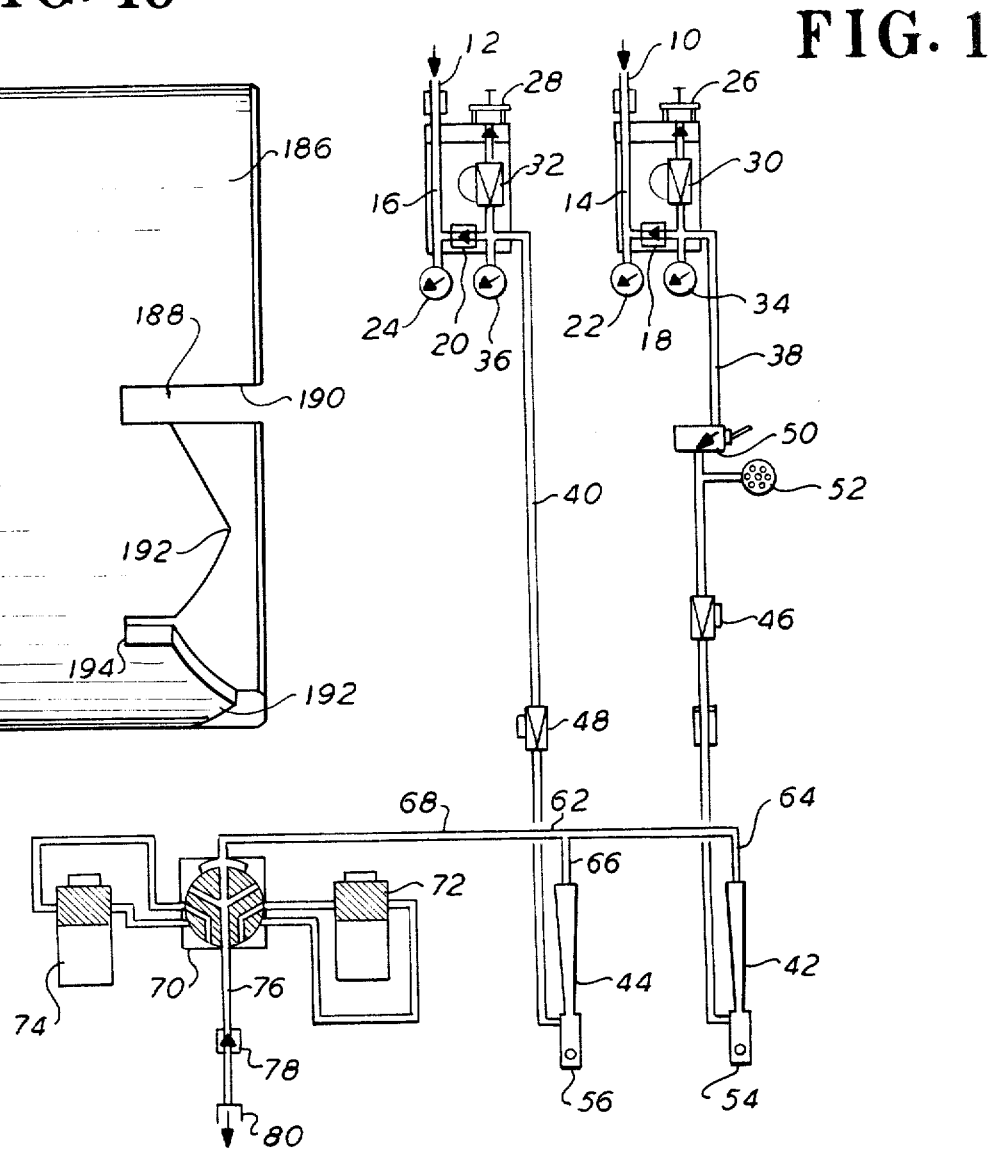
FIG. 1 is a schematic view of a typical flow path for an anesthesia machine and depicting the selector valve of the present invention.
FIG. 2 is a schematic view of the selector valve used in FIG. 1 showing the same in a position wherein anesthetic vapor is being provided to a patient.
FIG. 10 is a side isometric view of a portion of the component of FIG. 7.

Referring particularly to FIG. 1, there is shown a schematic view of an anesthesia machine adapted to provide a mixture of oxygen and nitrous oxide to a patient for inducing anesthesia and utilizing a selector valve constructed in accordance with the present invention.

The machine includes an oxygen inlet 10 and nitrous oxide inlet 12 which are adapted to be connected to normal pipelines of those gases supplied in a hospital. Such pipeline systems are readily used in hospitals and typical line pressure for both nitrous oxide and oxygen is about 50 psi.

The gases, oxygen and nitrous oxide thus pass respectively through suitable inlet tubes 14, 16 and check valves 18, 20 and the pressure in each of the pipelines can be read by gages 22 and 24.

In the event pipeline gases encounter a failure, or in some instances where pipeline gas is not available, suitable yokes, for oxygen and nitrous oxide, 26 and 28 are adapted to receive gas cylinders. The pressures are then regulated by regulators, respectively, 30 and 32, and the pressures read by gages 34 and 36.

Main conduits 38 and 40 feed, respectively, the oxygen and nitrous oxide to flowmeters 42 and 44 where a visual indication of the flow of the two gases may be continuously monitored by the user.

Pressure regulators 46 and 48 are located in the conduits 38 and 40 and, in oxygen conduit 38, there may also be a main oxygen shutoff valve 50 and an indicator 52 which notifies the user whenever the machine is on.

Carrying out the remaining components of the anesthesia machine, at the inlets to the oxygen flowmeter 42 and the nitrous oxide flowmeter 44 are needle valves, respectively 54 and 56 which are normally adjusted by the user to choose whatever flow and proportions of nitrous oxide and oxygen are desired in the eventual mixture. The user is, of course, guided in such adjustment by the visual monitoring of the flow of each of the gases by the individual flowmeters 42 and 44.

The gases thus mix in a confluence at 62 when tubes 64 and 66 meet, each carrying its particular gas.

The mixed gas of nitrous oxide and oxygen thereafter proceeds through tubing 68 into a selector valve 70 made and operated in accordance with the present invention.

In FIG. 1, the selector valve 70 is shown in schematic form wherein the various flow paths may be seen. A pair of calibrated type vaporizers 72 and 74 provide the introduction of a volatile liquid anesthetic, when desired, into the flow of gases to a patient.

As shown in FIG. 1, the selector valve 70 is in the intermediate position where gas from tubing 68 passes directly through selector valve 70 to an outlet tubing 76, check valve 78 and thereafter is administered to the patient via some means such as a face mask 80.

In such position, there is no flow of the gas from tubing 68 through either of the vaporizers 72, 74 and thus the patient is receiving only pure oxygen or a mixture of nitrous oxide and oxygen.

In FIG. 2, there is shown, in schematic, the selector valve 70 where the vaporizer 72 has been selected for use and thus a path for the flow of gas is provided from tubing 68, through the selector valve 70 while passing through vaporizer 72 when a desired amount of the volatile liquid anesthetic is picked up and which then passes through the outlet tubing 76 to the patient. As may also be seen, the remaining vaporizer 74 is completely out of the circuit or path of gas to a patient such that no gas leaves the selector valve 70 toward vaporizer 74 and also any vapor that may be present in vaporizer 74 cannot pass via any path from the selector valve 70 to any other path. The vaporizer 74 is therefore completely closed off and no anesthetic vapor from vaporizer 74 may inadvertently enter, through seepage or the like, into the stream of gas to the patient.

Figure 3:
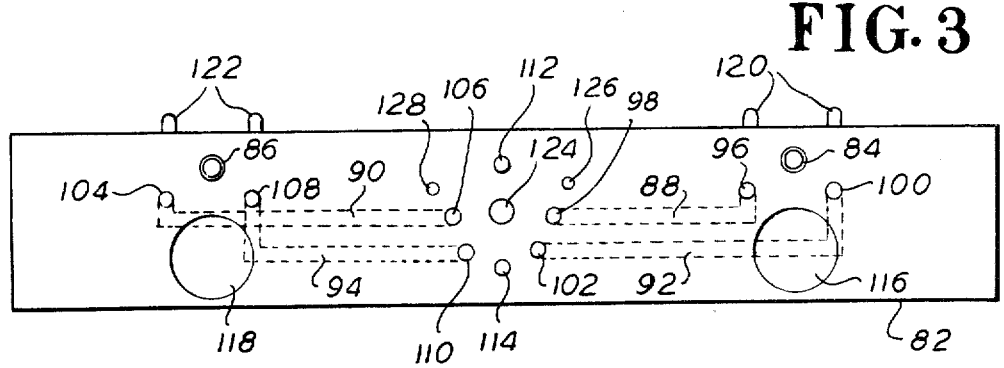
FIG. 3 is a front view of the manifold of an anesthesia machine constructed in accordance with the present invention.

Referring now to FIG. 3, a manifold 82 is shown on which is adapted to be mounted the vaporizers 72 and 74 (not shown in FIG. 3). Basically, the manifold 82 has a mounting means for each of the vaporizers 72 and 74, particularly, there are drilled holes 84 and 86 for each such mounting, such that each vaporizer is mounted to the front surface of manifold 82 and secured thereto by a bolt, not shown, that enters the rear of manifold 82 and is threaded into a corresponding hole in the back of each such vaporizer. The vaporizer has suitable fittings that enter in a gastight relationship with passageways in the manifold, as shown, manifold inlet passageways 88,90 and manifold outlet passageways 92,94. Each of the aforesaid passageways are formed within the manifold 82 and serve to carry gas to and from the vaporizers 72 and 74 as will be described.

When the vaporizers are mounted to manifold 82, the vaporizer 72 has an inlet that abuts the vaporizer inlet opening 96, within the manifold 82 and which communicates with manifold inlet passageway 88. At the other end of manifold inlet passageway 88, there is an opening 98 that, as will be shown, communicates with passageways within selector valve 70.

Similarly, the manifold outlet passageway 92 has one end ending in a vaporizer outlet opening 100 and which receives gas and anesthetic vapor from vaporizer 72 when that vaporizer is in use. The other end of manifold outlet passageway 92 terminates in an opening 102 that again is used, as will be explained, in connection with certain flow paths within the selector valve 70.

In similar manner, with respect to vaporizer 74, the manifold inlet passageway 90 has a vaporizer inlet opening 104 that aligns with the inlet of vaporizer 74 when the same is mounted upon manifold 82. At the other end of manifold inlet passageway 90 there is an opening 106 that receives gas from the selector valve 70 when vaporizer 74 is on stream. The manifold outlet passageway 94 within manifold 82 has a vaporizer outlet opening 108 that receives gas and liquid anesthetic vapor when vaporizer 74 is on stream and such gas/vapor is conveyed to opening 110 at the opposite end of manifold outlet passageway 94.

The manifold 82 further has a manifold inlet 112 which receives gas from tubing 68 (FIG. 1) and a manifold outlet 114 which delivers gas from the manifold 82 to outlet tubing 76 (FIG. 1).

Completing the description of manifold 82, there are two pairs of upwardly directed pins 120,122 upon which the vaporizers 72 and 74 are hung in mounting the same to the manifold 82. In addition, a central drilled hole 124 is located in about the center of the manifold 32, and at the center of a circle that intersects each of the openings 98, 102, 106, 110 and the manifold inlet 112 and manifold outlet 114 in manifold 82. In addition, protruding from manifold 82 and on a circle having the same center as the central drilled hole 124 but at a different radius as openings 98, 102, 106, 110 and manifold inlet and outlet 112, 114 are positioning pins 126 and 128 which serve to align the selector valve 70 in predetermined exact position with respect to the openings in manifold 82, such that the flow paths of gases to and from the selector valve 82 are unobstructed.

Figure 4:
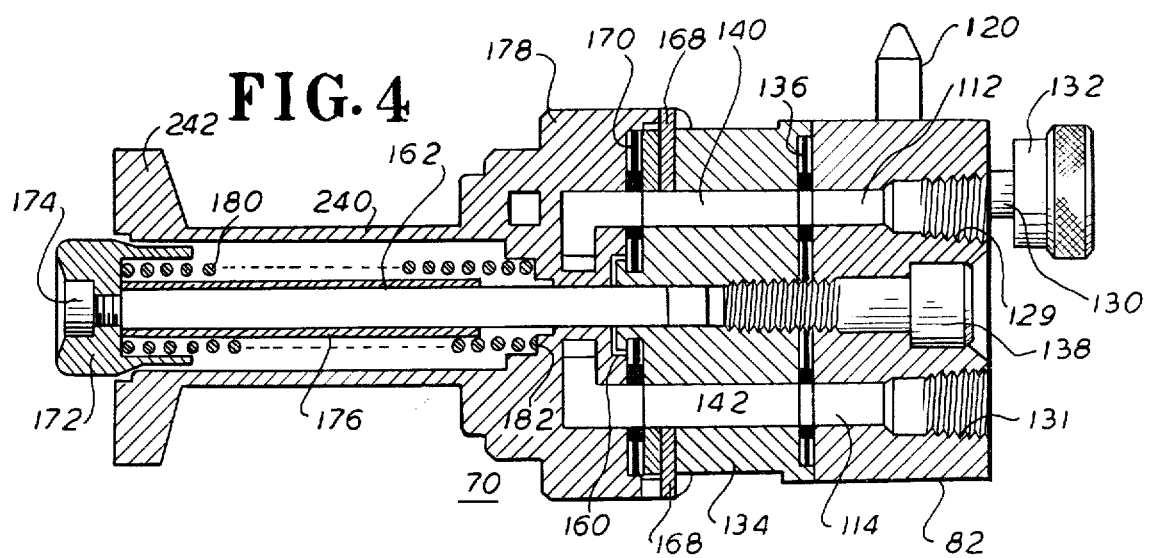
FIG. 4 is a side cross-sectional view of the selector valve of the present invention.

Turning now to FIG. 4, there is shown a cross-sectional view of a selector valve 70 mounted on manifold 82. As shown, manifold 82 has a threaded connection 129 which is adapted to receive a suitable fitting for introducing gas for tubing 68 (FIG. 1) to the manifold 82 to communicate such gas to the manifold inlet 112. Similarly, a threaded connection 131 interfits with outlet tubing 76 (FIG. 1) to receive gas from the manifold outlet 114.

Also shown in FIG. 4 as a part of manifold 82 is a typical pin 120 for mounting a vaporizer and a bolt 130 having a knurled knob 132 which fits through drilled hole 84 (FIG. 3) for retaining a vaporizer to the manifold 82.

Mounted to the manifold 82 is the selector valve base 134 which is circular and which is sealed to the manifold 82 by a single elastomeric seal 136. A cap screw 138 which fits within a recess in the manifold 82 is threaded into the selector valve base 134 and, when tightened, clamps the selector valve base 134 to the manifold 82 and compresses elastomeric seal 136 to a predetermined thickness.

Figure 6:
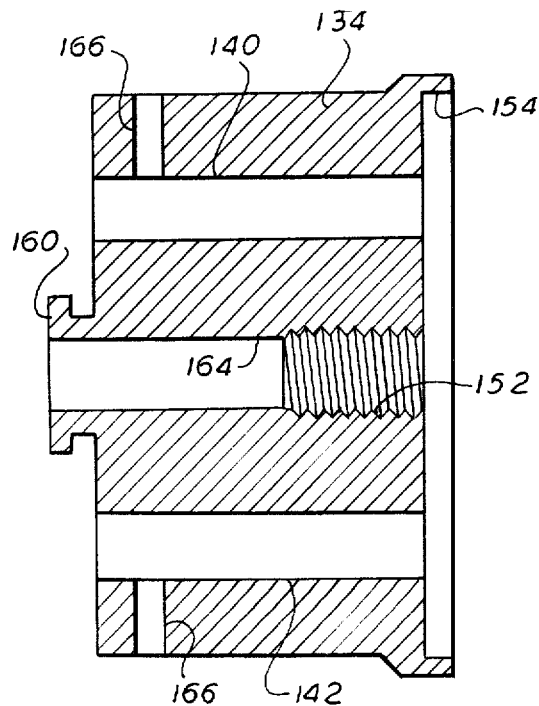
FIG. 6 is a cross-sectional view of the component of FIG. 5 taken along the lines 6—6.
Figure 5:
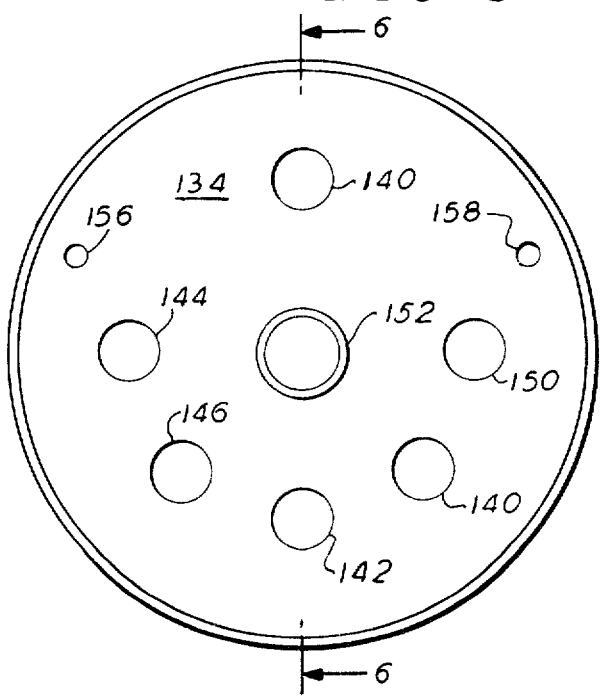
FIG. 5 is an end view of one of the components of the selector valve of FIG. 4.

The selector valve base 134 is more fully shown in FIGS. 5 and 6 wherein FIG. 5 shows an end view of base 134 as that face bears against elastomeric seal 136 and wherein FIG. 6 is a cross-sectional view of the selector valve base 134 taken along the lines 6—6 of FIG. 5.

In FIG. 5, there is shown a series of drilled holes in the selector valve base 134. Specifically, base inlet 140 aligns with manifold inlet 112 whereas base outlet 142 aligns with manifold outlet 114. In similar fashion, when selector valve base 134 is installed to manifold 82 as shown in FIG. 4, the base holes 144, 146, 148 and 150 align, respectively, with openings 98, 102, 110 and 106 (FIG. 3) of the manifold 82. A center threaded hole 152 is also provided to receive cap screw 138 as described in FIG. 4. A recess 154 (FIG. 6) is provided in selector valve base 134 in order to retain the elastomeric seal 136. The actual alignment of the selector valve base 134 to the manifold 82 is accomplished by the positioning pins 126,128 (FIG. 3) which project outwardly from manifold 82 and enter the pin alignment holes 156,158, respectively, in the selector valve base 134.

The selector valve base 134 (FIGS. 4 and 6) further has a flanged projection 160 and joined to the base 134 by a press fit, is a cylindrical stem 162 which is pressed within the central hole 164 of the selector valve base 134. Further drilled holes 166 are located in the selector valve base 134 and receive pins 168 as will be later explained.

A further elastomeric seal 170 (FIG. 4) is provided at the forward surface of the selector valve base 134 and is retained thereto by fitting the elastomeric seal 170 over the flanged projection 160 and may further be aligned by a plurality of pins (not shown) which project outwardly from selector valve base 134 and which fit into corresponding holes in the elastomeric seal 170.

At the extended end of the cylindrical stem 162, there is located at knob 172 which is fastened to the cylindrical stem 162 by means such as a cap screw 174.

A tubular stop 176 is loosely fitted about cylindrical stem 162 and serves to limit the movement of a rotor 178 as it slides laterally with respect to cylindrical stem 162, as will be later explained.

A compression spring 180 surrounds the tubular stop 176 and has one end thereof bearing against the knob 172 and the other end bearing against a recess 182 in the rotor 178, such that the compression spring 180 exerts a bias or continuous force which pushes the rotor 178 against elastomeric seal 170 and the selector valve base 134.

The rotor 178 is shown in more detail in FIGS. 7, 8, 9, and 10 and, as will be initially described, the selector valve 70 will be in the bypass position, or that shown in FIG. 1 wherein gas passes through the selector valve 70 directly to the patient and does not pass through either of the two vaporizers 72 or 74.

As noted, FIG. 8 is a cross-sectional view of the rotor 178 taken along the lines 8—8 of FIG. 7 and FIG. 9 is a cross-sectional view of the rotor 178 taken along the lines 9—9 of FIG. 7. FIG. 10 is a side isometric view of a portion of rotor 178.

The rotor 178 has three positions as explained with respect to FIGS. 1 and 2. In its center position (as shown in FIGS. 7-10) the gas passes directly through the selector valve 70 to the patient and does not pass through either of the two vaporizers. In the other two positions of the selector valve 70, either one of the two vaporizers is placed in the circuit such that vapors from the volatile anesthetic are picked up and carried by the gas to the patient.

To achieve these three positions in a positive manner, the rotor 178 is turned, with respect to the selector valve base 134 to the three positions, wherein the middle position corresponds to the bypass position and the rotor 178 can be rotated to positions to the right and left of center position to select one of the two vaporizers.

The rotor 178 has a lower manifold 184 having a projecting flange 186 which is so shaped as to cooperate with the pins 168 to set the three positions of rotor 178. As shown, particularly in FIG. 10, the projecting flange 186 has a slot 188 which is indented from the outer edge of flange 186 to a predetermined inner depth. In the preferred embodiment, there are two slots 188, 180 degrees apart, and which determine the outer or furthest radial travel of the rotor 178, that is, in either position where a vaporizer is on stream. As may be seen with brief reference to FIG. 4, the rotor 178 is spring loaded against selector valve base 134, and can be pulled against the spring bias away from selector valve base 134 a limited distance, determined by the length of tubular stop 176. In doing so, the rotor 178 moves away from the pins 168, however, when in position when a vaporizer is on stream, the distance that the rotor 178 can move is limited by tubular stop 176 such that the pins 168 cannot be completely removed from the slots 188, thus the projecting flange 186, having a full slot face 190, prevents the rotor 178 from moving radially in one direction since the full slot face 190 blocks the pins 168.

In the other direction of movement, however, see FIG. 10, the projecting flange 186 is formed in a series of V-shaped cams 192, the uppermost portion of which is reduced with respect to the full slot face 190 and, therefore, pins 168 can pass thereby. A central slot 194 is located equidistant between slots 188 and, when the pins 168 are positioned within central slot 194, the rotor 178 is in its middle or bypass position. Obviously, since two pins 168 are used, 180 degrees apart, the slot 188, V-shaped cams 192 and central slot 194 have counterparts (not shown) 180 degrees apart formed in the projecting flange 186.

Thus, the rotor 178 has three definite and distinct positions, and spring bias forces the rotor 178 into one of the three positions when pins 168 are engaged in slots 188 or the central slot 194.

Because of the V-shaped cams 192, the rotor 178 cannot be left in any position intermediate the three positions described, otherwise the spring bias would cause the rotor 178 to turn such that the pins 168 would be forced into one of the slots 188 or central slot 194.

Turning again to FIGS. 7-10, the three positions and the differing flow paths in each position can now be explained.

The lower manifold 184 has a central hole 196 and eight equally spaced holes 198, 200, 202, 204, 206, 208, 210 and 212 on a radius equal to the radius of the openings 98, 102, 106 and 110 and manifold inlet and outlet 112 and 114 in the manifold 82 (FIG. 3). Each of the holes 198, 200, 202, 204, 206, 208, 210 and 212 open in the flat surface 214 of the lower manifold 184 and surround a recess 216 formed in the flat surface 214. The flat surface 214 faces elastomeric seal 170 and seals thereagainst when the selector valve 70 is in any one of its three positions.

As may be seen in FIG. 8, where the selector valve 70 is, as explained, in the bypass position, the hole 198 in lower manifold 184 lines up with the manifold inlet 112 (FIG. 1) in manifold 82 and base inlet 140 of the selector valve base 134 and thus gas through manifold inlet 112 can flow into hole 198 in the lower manifold 184. A circular groove 218 and radial slots 220 join holes 198 and 206 in the lower manifold 184, such that gas entering the manifold inlet 112 (FIG. 3 or 4) enters the lower manifold 184 as described and the gas thus passes through the circular groove 218 and leaves through hole 206 in the lower manifold 184 and then through base outlet 142 in the selector valve base 134 and passes through the manifold outlet 114 and thereafter to the patient.

Thus, in the mid-position, or bypass position, gas entering the manifold inlet 112 passes directly through the selector valve 70 to the manifold outlet 114 to the patient and, as will be shown, does not pass through either of the vaporizers.

The holes 202 and 204 in lower manifold 184 are also joined by means of arc-shaped slot 222 and holes 208 and 210 of lower manifold 184 are also joined by a similar arc-shaped slot 224.

The rotor 178 also includes an upper manifold 226 which may be soldered to the flat surface 228 of lower manifold 184. The upper manifold 226 has two holes 230 and 232 and which are in alignment with holes 212 and 200, respectively, in the lower manifold 184. An arc-shaped slot 234 in upper manifold 226 joins holes 230 and 232.

A washer 236 is affixed to the outer surface 238 of upper manifold 226 by means such as solder and a sleeve 240 depends outwardly from washer 236 and terminates in a knob 242.

The operation of the selector valve 70 is thus as follows:

The compression spring 180 biases the rotor 178 against elastomeric seal 170 and selector valve base 134 in each of the three operating positions, i.e. when pins 168 (FIG. 4) are seated in either of the slots 188 or the central slot 194. As explained, the action of the spring bias in connection with V-shaped cams 192 prevents the rotor 178 from being left in any but one of the three set positions.

In the middle, or bypass position, as was explained, the gas entering the manifold 82 through manifold inlet 112 passes through the selector valve 70 and exits via the manifold outlet 114 in the manifold 82 to the patient. In this position the openings 106 and 110 in manifold 82 (FIG. 3) are in communication, respectively, with holes 202 and 204 of the rotor 178 and the arc-shaped slot 222. Thus the passageways both to and from a vaporizer connected to vaporizer inlet opening 104 and vaporizer outlet opening 108 are completely isolated from the gas passing through the selector valve 70 and none of the vapors within such vaporizer can inadvertently stray into any other path through the selector valve 70. Such vaporizer is also seated from the atmosphere such that vapor cannot escape into the operating theatre when that vaporizer is not being utilized.

Similarly with respect to any vaporizer connected to vaporizer inlet opening 96 and vaporizer outlet opening 100 (FIG. 3) of manifold 82, the corresponding openings 98 and 102 leading from manifold 82 into selector valve 80 are aligned with holes 210 and 208 of the lower manifold 184 which are joined by arc-shaped slot 224, thus, any such vaporizer is also isolated from any other path of gas through selector valve 70 and from the atmosphere.

To change the selector valve 70 to either one of its other two positions, i.e. where one of the vaporizers is in the circuit, the rotor 178 is pulled away from the selector valve base 134 by pulling knob 242 (FIG. 4) against the bias of compression spring 180 to the limit of its travel as determined by tubular stop 176. Such movement frees the pins 168 from the central slot 194 such that the rotor 178 can be turned either clockwise or counterclockwise one position until the pins 168 hit one of the full slot faces 190, thus limiting rotation in that direction. Upon releasing knob 242, the compression spring 180 pushes the rotor 178 toward the selector valve base 134 and seals thereagainst by elastomeric seal 170 and the pins 168 engage in one of the slots 188.

Taking such rotation, for example, to have been in the counterclockwise direction, the gas stream enters by means of the manifold inlet 112 and enters the rotor 178 through hole 212 in lower manifold 184. The gas then passes into hole 230 in the upper manifold 226, through the arc-shaped slot 234 and back into the upper manifold hole 232 and re-enters the lower manifold 184 via hole 200. From the lower manifold hole 200 the gas passes into the manifold 82 (FIG. 3) through opening 106, manifold inlet passageway 90 and enters a vaporizer connected to vaporizer inlet opening 104. The gas then passes through the vaporizer, picking up the desired amount of anesthetic vapor and re-enters manifold 82 through vaporizer outlet opening 108, into manifold outlet passageway 94 and re-enters selector valve 70 through opening 110 in manifold 82 which aligns with hole 202 in lower manifold 184. The gas/vapor enters hole 202, passes through arc-shaped slot 222 and leaves the lower manifold 184 through hole 204 which, in the counterclockwise position, is aligned with base outlet 142 of selector valve base 134 and thus leaves the selector valve 70 through manifold outlet 114 in the manifold 82 to a patient.

When the rotor 178 is thus in the counterclockwise position wherein the vaporizer connected to vaporizer inlet opening 104 and vaporizer outlet opening 108 is in use, the other vaporizer which is connected to vaporizer inlet opening 96 and vaporizer outlet opening 100 is closed via manifold inlet passageway 88 and manifold outlet passageway 92 at holes 208 and 210 of the rotor 178 and 206 and 198 of the rotor 178, respectively. Thus both the inlet to that vaporizer and the outlet therefrom are closed at the selector valve base 134 of the selector valve 70 and no vapors from that vaporizer can enter the path of gas to the patient or can escape to the outside atmosphere.

As may now be seen, clockwise movement of the rotor 178 brings about the same result. In such case the vaporizer in the righthand position in FIG. 3 would be placed in the circuit, and both the manifold inlet and manifold outlet passageways for the other vaporizer would be closed at the selector valve base 134, thus again preventing the inadvertent escape of vapors from the vaporizer not in service to any other flow path of gas through the selector valve 70 or to the surrounding atmosphere.

It will be understood that the scope of the method and product of this invention is not limited to the particular steps or materials disclosed herein, by way of example, but only by the scope of the appended claims.

I claim:

1. In an anesthesia machine comprising two anesthetic vaporizers each having an inlet and an outlet, inlet means for receiving a gas, outlet means for delivering said gas to a patient and a three-position selector valve means for controlling the flow of gas between said inlet means, said anesthetic vaporizers and said outlet means, the improvement comprising: said selector valve means having two extreme positions where either of said two anesthetic vaporizers are utilized and a middle position where no anesthetic vaporizer is utilized, said selector valve means having an input port communicating with said inlet means for receiving gas and an output port communicating with said outlet means for delivering a gas to a patient, said selector valve having a first intermediate inlet and outlet communicating, respectively, with the outlet and inlet of one of said vaporizers for providing a path of gas to said one vaporizer and receiving gas therefrom, and a second intermediate inlet and outlet communicating, respectively, with the outlet and inlet of the other of said vaporizers for providing a path of gas to said other vaporizer and receiving gas therefrom, said selector valve means providing a first flow path for gas received in said input port directly to said output port when said selector valve is in the middle position and further closing said first and second intermediate inlets and outlets to isolate said vaporizers from said direct path and from each other, a second flow path for gas received in said input port to said one of said vaporizers and to said output port when said selector valve is in one of said extreme positions and, a third flow path for gas received in said input port to said other of said vaporizers and to said output port when said selector valve is in the other of said extreme positions.

2. In an anesthesia machine as defined in claim 1 wherein said vaporizers are isolated by communicating said first intermediate inlet with said first intermediate outlet and communicating said second intermediate inlet with said second intermediate outlet when said valve is in said middle position.

3. In an anesthesia machine as defined in claim 1 wherein when said valve selector means is in one of said extreme positions, said first intermediate inlet and said first intermediate outlet are respectively connected to the inlet and outlet of said one vaporizer and whereby gas communicates therethrough from said selector valve means to said one of said vaporizers and returns therefrom, and wherein said second intermediate inlet and said second intermediate outlet are respectively disconnected from said inlet and outlet of said other vaporizer to isolate said other vaporizer from the path of any gases through said selector valve means.

4. In an anesthesia machine as defined in claim 1 wherein said selector valve means comprises a base and a rotor rotably mounted in said base and movable to any one of said three positions, said base having at least one pin projecting outwardly therefrom, said rotor having a plurality of recesses that receive said at least one pin, thus providing positive positions of said rotor.

5. In an anesthesia machine as defined in claim 4 wherein said rotor is biased towards said base and is movable away from said base against said bias to move said rotor to one of its three positions wherein said at least one pin is received in at least one of said plurality of recesses.

6. In an anesthesia machine as defined in claim 4 wherein the rotor surface intermediate any two adjacent of said plurality of recesses is a V-shaped cam such that said bias causes said at least one pin to move along the surface of said V-shaped cam to seat in at least one of said plurality of recesses.

* * * * *